US012729131B2

(12) United States Patent
Mino et al.

(10) Patent No.: US 12,729,131 B2
(45) Date of Patent: Sep. 8, 2026

(54) PIGMENT COMPRISING PARTICLES EACH CONTAINING CALCIUM-TITANIUM COMPOSITE OXIDE AS MAIN COMPONENT, METHOD FOR PRODUCING SAME, AND USE OF SAME

(71) Applicant: Titan Kogyo Kabushiki Kaisha, Yamaguchi (JP)

(72) Inventors: Wataru Mino, Yamaguchi (JP); Naotaka Shimomura, Yamaguchi (JP); Chihiro Nada, Yamaguchi (JP)

(73) Assignee: Titan Kogyo Kabushiki Kaisha, Yamaguchi (JP)

( * ) Notice: Subject to any disclaimer, the term of this patent is extended or adjusted under 35 U.S.C. 154(b) by 459 days.

(21) Appl. No.: 18/254,946

(22) PCT Filed: Oct. 15, 2021

(86) PCT No.: PCT/JP2021/038235
§ 371 (c)(1),
(2) Date: May 30, 2023

(87) PCT Pub. No.: WO2022/113560
PCT Pub. Date: Jun. 2, 2022

(65) Prior Publication Data

US 2024/0051840 A1 Feb. 15, 2024

(30) Foreign Application Priority Data

Nov. 30, 2020 (JP) ................................ 2020-198705

(51) Int. Cl.

| | |
|---|---|
| ***C01G 23/00*** | (2006.01) |
| ***A61K 8/29*** | (2006.01) |
| ***A61Q 1/02*** | (2006.01) |
| ***A61Q 17/04*** | (2006.01) |
| ***C08K 3/22*** | (2006.01) |
| ***C09C 1/36*** | (2006.01) |
| ***C09D 7/61*** | (2018.01) |
| ***C09D 11/037*** | (2014.01) |

(52) U.S. Cl.
CPC .............. *C01G 23/006* (2013.01); *A61K 8/29* (2013.01); *A61Q 1/02* (2013.01); *A61Q 17/04* (2013.01); *C08K 3/22* (2013.01); *C09C 1/36* (2013.01); *C09D 7/61* (2018.01); *C09D 11/037* (2013.01); *C01P 2002/74* (2013.01); *C01P 2004/04* (2013.01); *C01P 2004/12* (2013.01); *C01P 2004/62* (2013.01); *C01P 2006/10* (2013.01); *C08K 2003/2237* (2013.01); *C08K 2201/003* (2013.01); *C08K 2201/005* (2013.01); *C08K 2201/011* (2013.01)

(58) Field of Classification Search
CPC .... C01G 23/006; A61K 8/29; A61K 2800/43; A61K 2800/651; A61K 8/0241; A61K 8/19; A61Q 1/02; A61Q 17/04; A61Q 1/12; A61Q 1/00; C08K 3/22; C08K 2003/2237; C08K 2201/003; C08K 2201/005; C08K 2201/011; C08K 9/02; C08K 9/04; C08K 2003/2206; C08K 2003/2241; C09C 1/36; C09C 1/3653; C09C 1/0081; C09C 1/02; C09D 7/61; C09D 11/037; C09D 7/62; C09D 11/322; C01P 2002/74; C01P 2004/04; C01P 2004/12; C01P 2004/62; C01P 2006/10; C01P 2002/72; C01P 2004/51; C01P 2004/84; C01P 2002/70; C01P 2004/54
See application file for complete search history.

(56) References Cited

U.S. PATENT DOCUMENTS

| | | | | |
|---|---|---|---|---|
| 5,223,559 | A | 6/1993 | Arraudeau et al. | |
| 12,065,571 | B2 * | 8/2024 | Mino | C09C 3/063 |
| 12,084,354 | B2 * | 9/2024 | Seki | G03G 9/09716 |
| 2008/0047470 | A1 * | 2/2008 | Pfaff | C03C 1/04 106/417 |
| 2009/0060856 | A1 | 3/2009 | Katsuyama et al. | |

(Continued)

FOREIGN PATENT DOCUMENTS

| | | | | |
|---|---|---|---|---|
| CN | 106745214 A | 5/2017 | | |
| EP | 0983322 B1 | 7/2005 | | |
| EP | 1423486 B1 * | 10/2006 | | E04F 13/02 |

(Continued)

OTHER PUBLICATIONS

Machine Translation for WO 2020/017419 A1; published Jan. 23, 2020.*

(Continued)

*Primary Examiner* — Jeffrey T. Palenik
(74) *Attorney, Agent, or Firm* — COZEN O'CONNOR

(57) ABSTRACT

Provided are: a pigment through which light in a warm color region can pass preferentially and which has high hiding power and is mainly used in cosmetic applications; a method for producing the pigment; and a method for using the pigment. The pigment comprises particles each containing a calcium-titanium composite oxide as a main component, in which it is confirmed that regions each having a paler color than the color of a region surrounding thereof are scattered in a dot-like form in the particles when the particles of the calcium-titanium composite oxide in the pigment are observed in a transmission electron microscopic image at a magnification of 100,000×, and the true density of the pigment is 3500 kg/m$^3$ to 3790 kg/m$^3$, inclusive.

12 Claims, 2 Drawing Sheets

(56) References Cited

U.S. PATENT DOCUMENTS

| | | | |
|---|---|---|---|
| 2018/0371257 | A1 | 12/2018 | Hata |
| 2019/0175457 | A1 | 6/2019 | Kim et al. |

FOREIGN PATENT DOCUMENTS

| | | | |
|---|---|---|---|
| JP | H05339121 | A | 12/1993 |
| JP | 2584562 | B2 | 2/1997 |
| JP | 10-167929 | A | 6/1998 |
| JP | 3464564 | B2 | 11/2003 |
| JP | 2007-327059 | A | 12/2007 |
| JP | 2008-056535 | A | 3/2008 |
| JP | 4684970 | B2 | 5/2011 |
| JP | 5363696 | B2 | 12/2013 |
| JP | 6258462 | B2 | 1/2018 |
| JP | 2020011857 | A | 1/2020 |
| KR | 20180117759 | A | 10/2018 |

OTHER PUBLICATIONS

International Application No. PCT/JP2021/038235, International Search Report mailed Dec. 21, 2021, 4 pages.

* cited by examiner

PIGMENT COMPRISING PARTICLES EACH CONTAINING CALCIUM-TITANIUM COMPOSITE OXIDE AS MAIN COMPONENT, METHOD FOR PRODUCING SAME, AND USE OF SAME

This application is a national stage application of PCT/JP2021/038235 filed on August Oct. 15, 2021, which claims priority to Japanese App. No. 2020-198705, filed on Nov. 30, 2020, the entirety of which is incorporated herein by reference.

TECHNICAL FIELD

The present invention relates to a pigment including particles containing a calcium-titanium composite oxide as a main component, and particularly to the pigment having a warm color light-transmitting effect as well as a high concealing strength.

BACKGROUND ART

Conventionally, make-up cosmetics, such as a foundation, contain colorants such as titanium oxide pigments, which have a large tinting strength, as well as other inorganic pigments and organic pigments in order to change skin tone for the purpose of covering up redness, dullness, spots, freckles, and the like of the skin to give a uniform and beautiful skin appearance.

As the titanium oxide, a pigment having a high concealing strength is typically used to give a uniform skin tone. When a pigment having a low concealing strength is used in a cosmetic, a large amount of the pigment needs to be added to exhibit a sufficient concealing strength, which causes the usability of the cosmetic to deteriorate. Japanese Patent No. 2584562 (Patent Literature 1) proposes a cosmetic containing spherical or elliptical titanium dioxide, which has a concealing strength.

However, when a foundation or a concealer containing titanium oxide having a high concealing strength is applied to the skin as a cosmetic, the intensity of scattered white light tends to be too strong, and thus the finish of the makeup is likely to be an unnatural pale color, resulting in the problem of so-called "white cast".

One way to prevent the white cast phenomenon is to use a rutile-type titanium oxide having a specific shape to balance the tinting and concealing strengths with the intensity of the scattered white light. For example, Japanese Patent No. 4,684,970 (Patent Literature 2) describes blending, into a cosmetic, an aggregate of fan-shaped rutile titanium oxide particles in which rod-shaped primary particles are aggregated and/or bound. Further, Japanese Patent No. 6258462 (Patent Literature 3) describes blending, into a cosmetic, a rutile-type titanium dioxide powder obtained by baking rutile-type titanium dioxide having needle-like projections on the particle surface.

Another way to prevent the white cast phenomenon is to use the scattering of light in the warm color range inside the skin. Japanese Patent No. 5,363,696 (Patent Literature 4) describes a study focused on a light propagating inside the bare skin. Specifically, the following is described: in a light scattering medium such as the skin, a part of the light irradiated on the skin penetrates into the interior, and is reflected by internal scattering bodies, whereby the light is emitted even from sites different from the irradiated sites. Using a colorant with a low absorptivity of light in the wavelength range of 630 nm to 700 nm in the skin cosmetic can make the distribution of the emission sites similar to that of bare skin and provide a natural texture.

However, in recent years, there has been a growing movement, mainly in Europe, to reduce the amount of titanium(IV) oxide, including rutile-type titanium oxide, and to use substitute materials, because its possibility of a hazard to health cannot be denied. Japanese Patent Laid-Open No. H05-339121 (Patent Literature 5) proposes the use of compounds having a perovskite crystal structure, such as calcium titanate, strontium titanate, barium titanate, calcium zirconate, and strontium zirconate, as pigments other than rutile-type titanium oxide. Japanese Patent No. 3464564 (Patent Literature 6) also describes an ultraviolet protection cosmetic containing particles of a complex oxide having a perovskite structure or a solid solution thereof.

CITATION LIST

Patent Literature

PTL 1: Japanese Patent No. 2584562
PTL 2: Japanese Patent No. 4684970
PTL 3: Japanese Patent No. 6258462
PTL 4: Japanese Patent No. 5363696
PTL 5: Japanese Patent Laid-Open No. H05-339121
PTL 6: Japanese Patent No. 3464564

SUMMARY OF INVENTION

Technical Problem

However, Patent Literature 5 discusses only lubricity, adhesion, and covering strength, and does not take into account the white cast phenomenon. In addition, Patent Literature 5 merely describes that a powder composed of particles made of a compound having a perovskite crystal structure, having an average particle size in the range of 0.05 to 15 μm, and having an equiaxed shape is added to a cosmetic. Patent Literature 5 does not describe a specific method of producing such a powder. Further, although Patent Literature 6 describes that a complex oxide powder represented by $CaTiO_3$ is synthesized, it does not describe a specific example in which this powder is added to a cosmetic. Moreover, although the ultraviolet-protecting effect, safety, and stability of a cosmetic containing a complex oxide having a perovskite structure are described, Patent Literature 6 does not look at countermeasures against the white cast phenomenon or at the concealing strength.

Although the development of substitutes for titanium oxide is progressing, the development of cosmetics that achieve a natural finish and have a high concealing strength is still in progress.

An object of the present invention is to provide a pigment that can be used as a substitute for titanium oxide, which preferentially transmits light in the warm color region to realize a natural finish and which also has a high concealing strength.

Solution to Problem

The present inventors have focused on calcium-titanium composite oxides as a substitute for titanium oxide, and as a result of intensive studies, have found that a pigment that includes particles containing a calcium-titanium composite oxide as a main component in which the presence of specific speckled marks can be confirmed when observed in a transmission electron microscopic image, and that has a true density in a specific range, preferentially transmits light in the warm color region and also has a high concealing strength.

The present invention includes, but not limited to, the following:

[1] A pigment comprising particles containing a calcium-titanium composite oxide as a main component, wherein when the particles of the calcium-titanium composite oxide in the pigment are observed in a transmission electron microscopic image at a magnification of 100,000×, portions lighter in color than surroundings can be confirmed to be present in a speckled manner in the particles, and the pigment has a true density of 3500 kg/m$^3$ or more and 3790 kg/m$^3$ or less.

[2] The pigment according to [1], wherein the portions lighter in color than the surroundings have a circular shape with a diameter of 1.5 nm or more and 15.0 nm or less or an elliptical shape with the longest axis length of 1.5 nm or more and 15.0 nm or less, and 100 or more and 200 or less of the portions lighter in color than the surroundings are present in a range corresponding to $1.0 \times 10^4$ nm$^2$ on the transmission electron microscopic image.

[3] The pigment according to [1] or [2], wherein the portions lighter in color than the surroundings have a number average of the diameter or the longest axis length of 2.5 nm or more and 4.5 nm or less.

[4] The pigment according to any one of [1] to [3], having a particle size of 200 nm or more and 500 nm or less.

[5] The pigment according to any one of [1] to [4], having a width of a particle size distribution set in JIS Z8825:2013 is smaller than 10.00.

[6] The pigment according to any one of [1] to [5], wherein, when the pigment is measured in X-ray diffractometry, and when an integrated diffraction intensity of a (1 2 1) plane appearing in a range of a diffraction angle of 32.50° or more and 33.50° or less is defined as 100.0, a ratio of an integrated diffraction intensity of a diffraction line appearing in a range of a diffraction angle of 24.75° or more and 28.00° or less is 12.00 or less.

[7] The pigment according to any one of [1] to [6], wherein a coating layer of an inorganic substance and/or an organic substance is present on at least a part of a surface of the particles.

[8] A method for producing the pigment according to any one of [1] to [7], the method including:

providing an aqueous solution containing a titanium source and a calcium source;

heating the aqueous solution to react the titanium source with the calcium source to produce a reaction product;

subjecting the reaction product to a calcium removal treatment and then solid-liquid separation to collect a solid; and heating the solid.

[9] A method for producing the pigment according to any one of [1] to [7], the method including:

mixing an acid deflocculant of a hydrolyzate of a titanium compound, an alkali, and a water-soluble compound containing calcium to obtain a mixture, and heating the mixture to 70° C. or higher and 100° C. or lower under atmospheric pressure to produce a reaction product;

cooling the obtained reaction product, followed by allowing to stand at pH 7.0 or less for 1 hour or more;

subjecting the reaction product after allowed to stand to solid-liquid separation to collect a solid; and firing the solid at 500° C. or higher.

[10] A cosmetic comprising the pigment according to any one of [1] to [7].

[11] A resin composition comprising the pigment according to any one of [1] to [7].

[12] A paint comprising the pigment according to any one of [1] to [7].

[13] An ink comprising the pigment according to any one of [1] to [7].

Advantageous Effects of Invention

The pigment obtained by the present invention, which includes particles containing a calcium-titanium composite oxide as a main component, preferentially transmits light in a warm color region and also has a high concealing strength.

When the pigment obtained by the present invention, which includes particles containing a calcium-titanium composite oxide as a main component, is used as a material, in particular, for a cosmetic, such as a foundation, that is applied to a skin, a cosmetic that can achieve a natural finish by scattering a transmitted light in a warm color range inside the skin, and has a high concealing strength can be obtained.

The pigment obtained by the present invention can also be used as a substitute for titanium oxide. Since the calcium-titanium composite oxide used in the pigment of the present invention has a UV-blocking effect equivalent to that of titanium oxide, it can be used in sunscreen creams and the like.

The pigment obtained by the present invention can be used in a wide range of applications in fields other than cosmetics by utilizing its ability to transmit light in a warm color range and its high concealing strength. Examples of such applications include, but are not limited to, adding to a resin to form a resin composition having a warm color light-transmitting effect and adding to a paint for use in residential paints.

DESCRIPTION OF EMBODIMENTS

The present invention relates to a pigment comprising particles containing a calcium-titanium composite oxide as a main component, wherein when the particles of the calcium-titanium composite oxide in the pigment are observed in a transmission electron micrograph at a magnification of 100,000×, portions lighter in color than surroundings can be confirmed to be present in a speckled manner in the particles, and the pigment has a true density of 3500 kg/m$^3$ or more and 3790 kg/m$^3$ or less.

"Pigment comprising particles containing a calcium-titanium composite oxide as a main component" means that the individual particles constituting the pigment are mainly calcium-titanium composite oxide particles. Specifically, this means that 850 g/kg or more, and preferably 900 g/kg or more, of the individual particles constituting the pigment are calcium-titanium composite oxide particles. In addition to the calcium-titanium composite oxide, the individual particles constituting the pigment of the present invention may include unreacted substances from a synthesis reaction of the calcium-titanium composite oxide, unavoidable impurities derived from raw materials, and inorganic substances and/or organic substances derived from a coating layer.

The calcium-titanium composite oxide, which is the main component of the particles constituting the pigment of the present invention, is preferably a calcium-titanium composite oxide having an orthorhombic crystal system. "Calcium-titanium composite oxide having an orthorhombic crystal system" refers to a calcium-titanium composite oxide in which the angles between three different crystal axes are all 90°.

Figure 1:
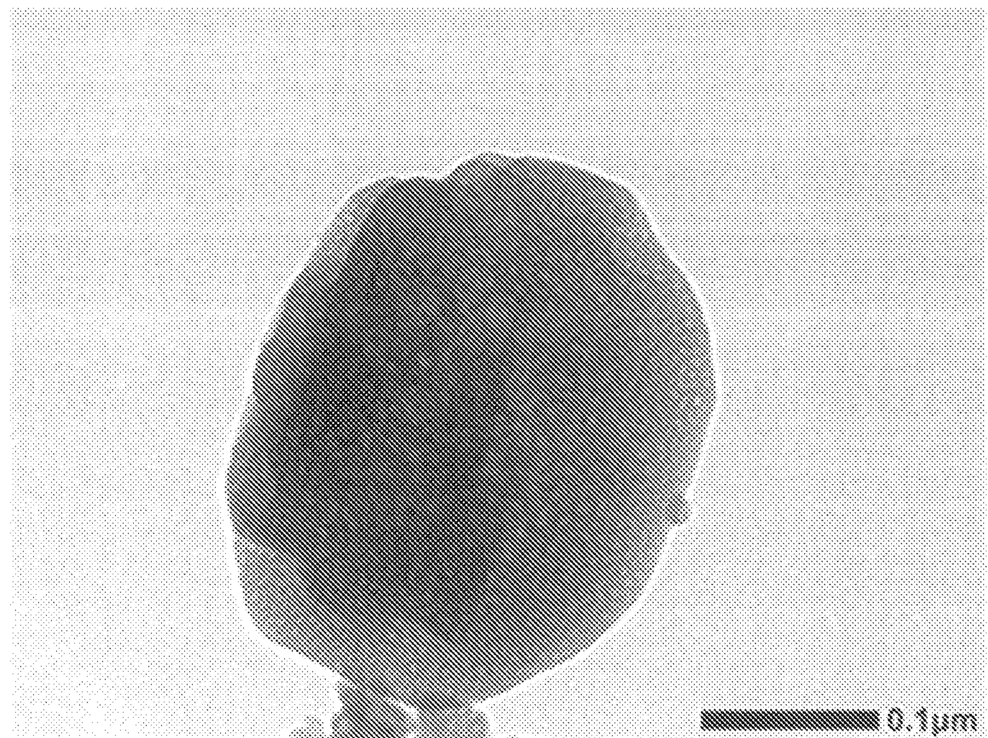
FIG. 1 is a transmission electron micrograph of the pigment obtained in Example 5.
Figure 2:
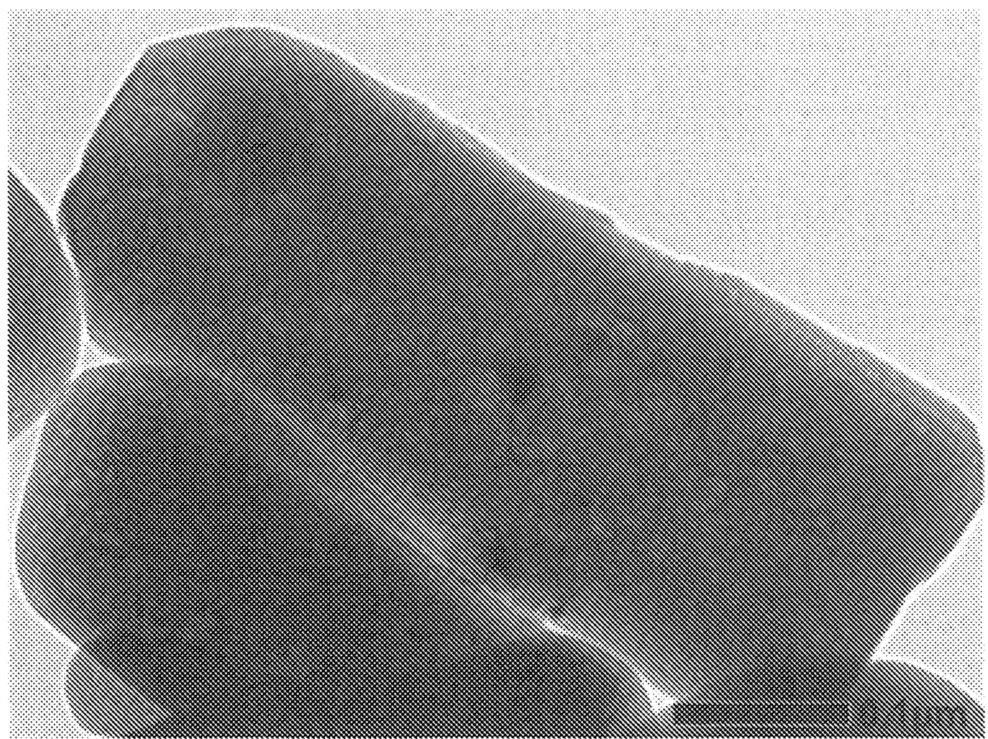
FIG. 2 is a transmission electron micrograph of the pigment obtained in Example 3.

As shown in FIGS. 1 and 2, the particles of the calcium-titanium composite oxide in the pigment of the present invention are characterized by the presence of dark and light portions within the particles in a transmission electron microscopic image. Specifically, when observed in a transmission electron microscopic image at a magnification of 100,000×, light-colored portions can be confirmed to be present in a speckled manner in dark-colored portions. The present inventors found that the warm color light-transmitting effect of the pigment is improved when speckled marks are observed in the calcium-titanium composite oxide particles. The relationship between the speckled marks and the effect of warm light transmission is not clear, but the reason why the effect is obtained is speculated to be as follows.

It is believed that the pigment of the present invention has voids inside the particles that were formed during the synthesis process. When the portions corresponding to the voids are observed with a transmission electron microscope, they appear lighter in color than the surroundings. Light having a short wavelength is easily scattered and reflected by such voids, and so it is believed that light in a warm color region is preferentially transmitted by the pigment of the present invention. In addition, it is believed that "voids" connected to other voids or the outside and "voids" that are not connected to other voids or the outside are both present.

Figure 3:
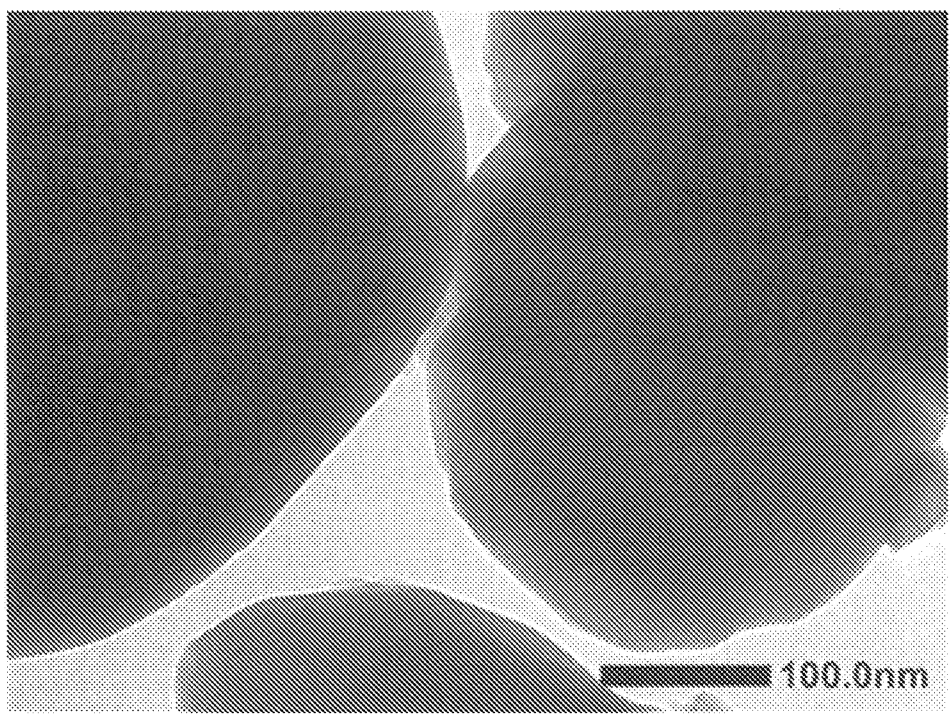
FIG. 3 is a transmission electron micrograph of the pigment obtained in Comparative Example 3.

The present inventors have found for the first time that calcium-titanium composite oxide particles in which speckled marks as described above are observed when observed in a transmission electron micrograph can be produced by the method described below. When a commercially available calcium-titanium composite oxide was observed with a transmission electron micrograph, no speckled marks were observed, as shown in FIG. 3.

The above-described speckled marks in the particles of the calcium-titanium composite oxide in the pigment of the present invention are desirably distributed in a uniform manner throughout the particles. However, in transmission electron micrographs, there are cases in which light-colored portions cannot be observed due to reasons such as the particles overlapping or the thickness of some particles being particularly large. If there is no particle-to-particle overlap, there is usually no particularly large increase in particle thickness at the outer edge of the particle. Therefore, for particles having speckled marks in the present invention, the speckled marks can usually be observed at least at the outer edge when observed in a transmission electron micrograph at a magnification of 100,000×. On the other hand, if there is no overlap between particles and speckled marks cannot be observed even at the outer edge of the particle in a transmission electron micrograph at a magnification of 100,000×, it can be judged that the particle does not have speckled marks.

Further, the pigment of the present invention is characterized in that it has a low true density as evaluated by the method described below. The true density of the pigment of the present invention is 3500 kg/m$^3$ or more and 3790 kg/m$^3$ or less. When the above-described speckled marks can be observed and the true density is 3790 kg/m$^3$ or less, in addition to the effect of transmitting warm light, an effect of improving the concealing strength can also be obtained. The level of the concealing strength depends on the shape of the particles themselves. Specifically, the rectangular parallelepiped particles described later tend to have a higher concealing strength than approximately spherical particles. However, when particles having the same shape as each other are compared, it was found that the particles having the speckled marks which can be observed in a transmission electron micrograph at a magnification of 100,000× and having the true density of 3790 kg/m$^3$ or less have greater concealing strength. Although the relationship between the true density and the improvement in the concealing strength has not been clarified, it is believed that when the true density is small, sufficient voids are formed inside the particles, and so light tends to be scattered and reflected more easily, which results in not only a warm light transmission effect, but also an effect of improving the concealing strength. If the true density is less than 3500 kg/m$^3$, the particles tend to disintegrate, and thereby usability as a material for cosmetics may deteriorate, and thus the true density is preferably 3500 kg/m$^3$ or more.

If the above-described light-colored portions present in a speckled manner have a circular shape with a diameter of 1.5 nm or more and 15 nm or less or an elliptical shape with a longest axis length of 1.5 nm or more and 15 nm or less, and there are 100 or more and 200 or less of such light-colored portions in a range corresponding to 1.0×10$^4$ nm$^2$ on the transmission electron micrograph at a magnification of 100,000×, the effect of a further improvement in the concealing strength can be seen when compared with particles having the same shape, and thus such characteristics are preferable. In addition, the number average diameter or the longest axis length (hereinafter collectively referred to as "number average diameter") is preferably 2.5 nm or more and 4.5 nm or less, more preferably 2.5 nm or more and 4.2 nm or less, and further preferably 3.0 nm or more and 4.2 nm or less. When the number average diameter of the particles is 2.5 nm or more, the concealment rate evaluated by the method described later tends to increase, and when the number average diameter of the particles is 4.5 nm or less, the particles tend to have structural stability. It should be noted that "circular" as used herein is not intended to be limited to a perfect circle, and is intended to include a shape close to a circle. The same is true for "elliptical".

Further, when 100 or more portions lighter in color than the surroundings are present in a range corresponding to 1.0×10$^4$ nm on the transmission electron microscopic image, it is thought that sufficient scattering of light having a short wavelength in the voids inside the particles occurs, light in the warm color region is preferentially transmitted, and the concealing strength of the pigment is improved. On the other hand, there is no further improvement in the concealing strength even if the number of such portions is more than 200. Further, when there are more than 200 of such portions, there are many voids in the particle, which may cause the particles to disintegrate, and usability as a material for cosmetics to deteriorate. Thus, the number of the above-described light-colored portions is preferably 200 or less.

The method for measuring the diameter or the longest axis length of the portions lighter in color than the surroundings on the transmission electron microscopic image at a magnification of 100,000×, and the specific method for measuring the number of portions lighter in color than the surroundings in the range corresponding to $1.0\times10^4$ $nm^2$ are described later.

In the pigment obtained by the present invention, the particles may have an approximately spherical shape or have a rectangular parallelepiped shape. "Approximately spherical" means that, as illustrated in FIG. 1, the primary particles or secondary particles are crystals that have grown isotropically or form aggregates isotropically, have an irregular outer shape or an outer shape similar to a sphere. For example, "approximately spherical" does not include a rectangular parallelepiped shape like that shown in FIG. 2, an elongated needle shape, or a shape like a sea urchin that has protrusions with a length equal to or longer than the diameter of the central part. "Rectangular parallelepiped" means that, as illustrated in FIG. 2, the primary particles or secondary particles have an outer shape close to a rectangular parallelepiped as a result of crystal growth preferential in a specific uniaxial direction than in the other two axes or as a result of aggregates preferentially formed in a specific uniaxial direction. "Rectangular parallelepiped" is not limited to a perfect rectangular parallelepiped in which all six faces are formed by rectangles or squares. Further, the shape of the cross-section of the particle perpendicular to the longest axis direction does not need to be rectangular or square, and the cross-sectional shape of all the cross-sections need not be the same shape.

"Particles have an approximately spherical shape" and "particles have a rectangular parallelepiped shape" mean that 80% by number or more, and preferably 85% by number or more, of the particles constituting the pigment of the present invention are approximately spherical and rectangular parallelepiped, respectively.

Pigments including approximately spherical particles are usually suitable for obtaining a smooth feel when used in a cosmetic. On the other hand, pigments including rectangular parallelepiped particles tend to have greater concealing strength than approximately spherical particles, and are suitable for obtaining a cosmetic that requires concealing strength.

When the pigment of the present invention has a rectangular parallelepiped shape, the advantage that a greater concealing strength than in the case of an approximately spherical shape can be obtained, but the pigment of the present invention is not limited to a rectangular parallelepiped shape. For example, when it is desired to make the particle shape of the pigment approximately spherical according to the desired texture of the cosmetic, a pigment using approximately spherical shaped particles having the characteristics of the present invention that "portions lighter in color than surroundings can be confirmed to be present in a speckled manner in the particles when the particles of the calcium-titanium composite oxide are observed in a transmission electron microscopic image at a magnification of 100,000×, and the true density is 3500 $kg/m^3$ or more and 3790 $kg/m^3$ or less" can be used as the pigment. In such a case, a greater concealing strength can be obtained as compared with an approximately spherical shaped particles that do not have the above characteristics.

The pigment of the present invention preferably has a particle size of 200 nm or more and 500 nm or less. When the particle size is within such a range, light scattering tends to occur and a high concealing strength tends to be obtained. The method for measuring the particle size of the pigment is described later.

The pigment of the present invention preferably has a narrow particle size distribution. If the width of the particle size distribution is large, the particle size becomes non-uniform, and when used in a cosmetic or the like, the filling rate decreases, and the concealing strength tends to decrease. The width of the particle size distribution is preferably 10.00 or less, more preferably 8.00 or less, and even more preferably 5.00 or less. The method for measuring the width of the particle size distribution of the pigment is described later.

It is desirable that the pigment of the present invention should have a small titanium oxide content because the pigment of the present invention may be used as a substitute for titanium oxide in cosmetics. To accurately calculate the content of titanium oxide in the calcium-titanium composite oxide, it is necessary to mix the pigment of the present invention and titanium oxide, and subject the resultant mixture to X-ray diffractometry by using a powder method to create a calibration curve. However, this method is time consuming and costly. Therefore, as a method for more easily confirming that the content of titanium oxide is small, an integrated diffraction intensity of a diffraction line appearing in the range of 24.75° or more and 28.00° or less, which has the highest integrated diffraction intensity of rutile, anatase, and brookite titanium oxides, may be compared with an integrated diffraction intensity of a diffraction line of the (1 2 1) plane appearing in the range of 32.50° or more and 33.50° or less, which is the highest integrated diffraction intensity of calcium-titanium composite oxide, in X-ray diffractometry by a powder method. In the present invention, when the integrated diffraction intensity of the diffraction line of the (1 2 1) plane appearing at 32.50° or more and 33.50° or less is defined as 100.0, it is preferable that a ratio of the integrated diffraction intensity of the diffraction line appearing in the range of 24.75° or more and 28.00° or less (hereinafter, referred to as "XRD titanium oxide integrated diffraction intensity") is 12.00 or less. When such a condition is satisfied, the content of titanium oxide in the pigment can be considered as being low. The XRD titanium oxide integrated diffraction intensity is more preferably 11.00 or less, and further preferably 8.50 or less. Since there is a diffraction line of the (1 1 1) plane of the calcium-titanium composite oxide in the range of 24.75° or more and 28.00° or less, and since the integrated diffraction intensity of the diffraction line of the (1 1 1) plane is about 3 when the integrated intensity of the diffraction line of the (1 2 1) plane is defined as 100.0, the above-described integrated diffraction intensity is not zero even if titanium oxide is not present at all.

The color of the pigment of the present invention is not particularly limited. However, since the pigment of the present invention may be used as a substitute for titanium oxide, it is preferably white like titanium oxide.

The pigment of the present invention may have a coating layer made of an inorganic material on the surface of the particles in order to impart hydrophobicity, optical properties, and the like. A coating layer made of an organic substance may be present. There may be two or more coating layers, or an inorganic coating layer and an organic coating layer may both be included.

The pigment of the present invention preferably has a warm color light-transmitting effect of 0.580 or more calculated by the method described later. When the warm color light-transmitting effect is 0.580 or more, reflection of light in the warm color range inside the skin is sufficient when the pigment is used in cosmetics, and a natural finish can thus be obtained. There is no particular upper limit for the warm color light-transmitting effect, and the theoretical maximum value of the warm color light-transmitting effect calculated by the evaluation method used in the present invention is 1.000.

The pigment obtained in the present invention preferably has a high concealing strength. When the concealment rate, which is an index of concealing strength, is evaluated by the method described later, the concealment rate of the pigment having approximately spherical particles is preferably 0.690 or more. A pigment having an approximately spherical particle shape and a concealment rate within the above range can impart a smooth feel and concealing strength to a cosmetic. A pigment having rectangular parallelepiped particles preferably has a concealment rate of 0.730 or more. A pigment having a rectangular parallelepiped particle shape and a concealment rate within the above range can impart a very high concealing strength to a cosmetic. There is no particular upper limit for the concealment rate, and the theoretical maximum value of the concealment rate calculated by the evaluation method used in the present invention is 1.00.

An example of the method for manufacturing the pigment of the present invention is shown below. However, the method for manufacturing the pigment of the present invention is not limited to the following.

A pigment that includes particles containing a calcium-titanium composite oxide as a main component and has the above-described features of the present invention can be produced by heating an aqueous solution containing a titanium source and a calcium source to react the titanium source with the calcium source to thereby produce a reaction product; subject the reaction product to a calcium removal treatment and then solid-liquid separation to recover a solid; and heat (fire) the obtained solid. The titanium source is preferably an acid deflocculant of a hydrolyzate of a titanium compound, and typically is an acid deflocculant of metatitanic acid obtained by a method called the sulfuric acid method. In the reaction between the titanium source and the calcium source, it is preferable to mix an alkali and heat the mixture to 70° C. or higher and 100° C. or lower at atmospheric pressure (atmospheric pressure heating reaction method). In the calcium removal treatment, it is preferable to cool the reaction product obtained by the atmospheric pressure heating reaction method, followed by allowing to stand at a pH of 7.0 or less for 1 hour or more. The obtained solid is preferably fired at 500° C. or higher.

(Sulfuric Acid Method)

Metatitanic acid represented by a chemical formula $TiO(OH)_2$ can be obtained by dissolving ilmenite ore with concentrated sulfuric acid, removing the resulting iron sulfate component, and carrying out a hydrolysis step.

(Atmospheric Pressure Heating Reaction Method)

Examples of the acid deflocculant of a hydrolyzate of a titanium compound, which is a representative example of the titanium source, include an acid deflocculant of metatitanic acid. As the metatitanic acid, it is preferable to use one obtained by using a compound having a sulfur content (in terms of $SO_3$) of 15 g/kg or less, and preferably 10 g/kg or less, as the hydrolyzate of a titanium compound, and deflocculating the hydrolyzate by adjusting the pH of the hydrolyzate to 0.8 or more and 1.5 or less using hydrochloric acid. By using an acid deflocculant of metatitanic acid obtained in such a way as the titanium source, it is possible to obtain calcium-titanium composite oxide particles having a small particle size distribution width. If the sulfur in the metatitanic acid exceeds 15 g/kg (in terms of $SO_3$), deflocculation may sometimes not progress. Nitric acid, hydrogen bromide, hydrogen iodide, formic acid, acetic acid or the like can also be used instead of hydrochloric acid. Further, instead of the acid deflocculant of a hydrolyzate of a titanium compound, a product obtained by neutralizing the deflocculant with an alkali can be used.

The calcium source (water-soluble compound containing calcium) is not particularly limited, and examples include calcium hydroxide and calcium carbonate.

Examples of the factors influencing the crystallinity and particle size of the pigment comprising particles containing a calcium-titanium composite oxide as a main component obtained by the atmospheric pressure heating reaction method include the concentrations and mixing ratios of the raw materials, the alkali concentration, the reaction temperature, and additives, etc. The mixing ratio between the titanium source and the water-soluble compound containing calcium is preferably such that the ratio of the amount of calcium (Ca element) to the amount of titanium (Ti element) is 1.00 or more and 1.60 or less, and more preferably 1.10 or more and 1.50 or less. The acid deflocculant of a hydrolyzate of a titanium compound used as a titanium source has a low solubility in water. Accordingly, when the amount of calcium is less than the amount of titanium, not only calcium-titanium composite oxide particles, but also unreacted titanium oxide tend to remain in the reaction product. The concentration of the acid deflocculant of a hydrolyzate of a titanium compound in the mixture in the atmospheric pressure heating reaction method is preferably, in terms of Ti, 0.5 mol/L or more and 1.5 mol/L or less, and more preferably 0.7 mol/L or more and 1.4 mol/L or less.

It is preferable to add an alkali in addition to the titanium source and the calcium source during the atmospheric pressure heating reaction. As the alkali, caustic alkali can be used, and sodium hydroxide is particularly preferable. The alkali concentration in the mixture during the atmospheric pressure heating reaction is preferably 0.1 mol/L or more, and more preferably in the range of 0.5 mol/L or more and 3.6 mol/L or less.

The higher the temperature during the reaction, the better the crystallinity of the product to be obtained. However, since a pressure vessel is required for the reaction at a temperature exceeding 100° C., the range of 70° C. or higher and 100° C. or lower is suitable for practical use, and the range of 70° C. or higher and lower than 100° C. is acceptable.

When the particles of the calcium-titanium composite oxide having approximately spherical shape is prepared, one or more sugars selected from monosaccharides and disaccharides such as glucose and maltose may be added as additives during the atmospheric pressure heating reaction. When any of sugars as described above are added, the total concentration thereof is preferably 0.0115 mole or more and 0.0195 mole or less, per mole of calcium added during the atmospheric pressure heating reaction. When the concentration is less than 0.0115 mol/mol, the particles may not become approximately spherical, and when the concentration is more than 0.0195 mol/mol, titanium oxide tends to remain. Further, in general, the particle size tends to be small when the amount of sugar added is large. In the case of using as a material for cosmetics, it is preferable that the particle size should not be too small, and so from this perspective the concentration of the sugar(s) to be added is preferably not more than 0.0195 mol/mol.

One or more compounds selected from aliphatic hydroxy acid compounds such as citric acid and isocitric acid may be added during the atmospheric pressure heating reaction. Adding an aliphatic hydroxy acid compound increases the aspect ratio of the particles of the calcium-titanium composite oxide. When adding the aliphatic hydroxy acid, the amount added is preferably 0.0180 mol or less per mol of calcium added during the atmospheric pressure heating reaction.

(Calcium Removal Treatment)

After synthesizing the calcium-titanium composite oxide by the atmospheric pressure heating reaction, it is preferable to carry out calcium removal treatment to prevent unreacted calcium from remaining and interfering with the surface treatment. The calcium removal treatment involves cooling the reaction product from the atmospheric pressure heating reaction to 55° C. or less and then adjusting the pH to 7.0 or less using an acid. More preferably, the pH is 6.0 or less. The lower limit of pH is preferably 2.5 or higher, and more preferably 4.5 or higher. Examples of the type of acids used for pH adjustment include hydrochloric acid, nitric acid, and acetic acid. If the pH is higher than 7.0, there is a possibility that unreacted calcium cannot be completely removed. On the other hand, if the pH is less than 2.5, calcium in the calcium-titanium composite oxide may flow out into the acid, whereby some titanium oxide may form.

(Firing)

After the calcium removal treatment, it is desirable to subject the reaction product to solid-liquid separation to collect the solid, and then fire the obtained solid. Although the concealing strength of the resulting pigment tends to improve as the firing temperature increases, firing at a temperature higher than 900° C. is not preferable because the voids inside the pigment particles may decrease. The firing temperature for producing the pigment of the present invention is preferably 500° C. or higher and 900° C. or lower.

(Surface Coating Treatment)

In the present invention, for the purpose of improving a dispersion stability and durability in a dispersion medium when manufacturing, for example, a cosmetic, the pigment of the present invention may be provided with a coating layer of an inorganic substance like a hydrous oxide or oxide of a metal such as aluminum, silicon, zinc, titanium, zirconium, iron, cerium, or tin on at least a part of the particle surface in the pigment. A metal salt other than those described above may be used for the inorganic coating. Further, to carry out a surface modification exemplified by a hydrophobic treatment, an organic coating layer may be provided on at least a part of the particle surface. Examples of organic coatings include treating with a silicone compound such as dimethylpolysiloxane and methylhydrogenpolysiloxane, a coupling agent such as a silane coupling agent, an aluminum coupling agent, a titanium coupling agent, and a zirconium coupling agent, a fluorine compound such as a perfluoroalkyl phosphate compound, a hydrocarbon, lecithin, an amino acid, polyethylene, a wax, and a metal soap, etc. A plurality of these treatments may be carried out in combination, and the order of the treatments is not particularly limited.

(Uses of Pigment)

The pigment of the present invention can preferentially transmit light in a warm color range, and so when used as a material for a cosmetic that is applied to a skin, the transmitted light in the warm color range scatters inside the skin, thereby suppressing white cast and thus enabling a natural finish. In addition, since the pigment of the present invention strongly scatters light other than the light in the warm color region, when the pigment is used as a cosmetic material applied to a skin, the pigment can cover up redness, dullness, spots, freckles, and the like in the skin, and can produce a uniform and beautiful skin appearance. Therefore, the pigment of the present invention can be suitably used as a material for a cosmetic. A cosmetic containing the pigment of the present invention is one aspect of the present invention. From another point of view, use of the pigment of the present invention as a material for cosmetics is also an aspect of the present invention. Further, use of the pigment of the present invention for suppressing a white cast phenomenon in cosmetics can also be said to be an aspect of the present invention. As used herein "the white cast phenomenon" refers to a phenomenon in which the finish of the makeup looks a pale color and unnatural in the case where the intensity of scattered white light is strong when the cosmetic is applied to a skin. "Suppressing a white cast phenomenon" means that the pigment of the present invention added to the cosmetic preferentially transmits light in a warm color range to occur scattering of the transmitted light in the warm color range inside the skin, thereby suppressing, reducing, or alleviating the above-described white cast phenomenon, and thus enabling a more natural makeup finish. As used herein, "light in a warm color range" refers to light with a wavelength of 570 nm or more and 780 nm or less.

The pigment of the present invention can also be used in a wide range of applications in fields other than cosmetics by utilizing its ability to transmit light in the warm color range. Examples of such applications include, but are not limited to, adding to a resin for use in sunroofs or the like and adding to a paint to form coating that transmits light in the warm color range. Further, the pigment obtained by the present invention can also be used as a substitute for titanium oxide.

(Cosmetic)

When using the pigment of the present invention as a material for a cosmetic, typically, the surface thereof may be coated as described above, and then the pigment may be mixed with an inorganic pigment and/or an organic pigment or the like according to a known method. The content of the pigment of the present invention in the cosmetic depends on the type of the cosmetic, and is not particularly limited. For example, for a powder type cosmetic about 1 g/kg or more and 900 g/kg or less of the pigment may be used, for an oily type cosmetic about 1 g/kg or more and 500 g/kg or less of the pigment may be used, and for an emulsion type or a cream type cosmetic about 1 g/kg or more and 150 g/kg or less of the pigment may be used. However, the pigment of the present invention is not limited to these ranges.

As the inorganic pigment and/or organic pigment that can be mixed when using the pigment of the present invention as a material for a cosmetic, inorganic pigments, organic pigments, and the like that are used in ordinary cosmetics may be used as necessary. Examples of such inorganic pigments include titanium oxide, zinc oxide, iron oxide represented by red iron oxide, cerium oxide, alumina, zirconium oxide, magnesium oxide, chromium oxide, magnesium silicate, magnesium aluminum silicate, calcium silicate, barium sulfate, magnesium sulfate, calcium sulfate, calcium carbonate, magnesium carbonate, talc, mica, surface-treated mica, a mica-like synthetic pigment, sericite, zeolite, kaolin, bentonite, clay, silicic acid, boron nitride, bismuth oxychloride, hydroxyapatite, ultramarine blue, Prussian blue, and dehydrates and complexes of these. Examples of organic pigments include silicone powder, elastic silicone powder, polyurethane powder, cellulose powder, nylon powder, urethane powder, silk powder, polymethyl methacrylate (hereinafter referred to as "PMMA") powder, polyethylene powder, starch, carbon black, metal soaps such as zinc stearate, and complexes of these. Tar dyes and various natural dyes can also be used.

The method for manufacturing the cosmetic is not particularly limited, and a known method may be used. The form of the cosmetic is also not particularly limited, and may be, for example, a powder, a solid powder, a cream, an emulsion, a lotion, an oily liquid, an oily solid, a paste, or the like. For example, the cosmetic may be a makeup cosmetic such as a makeup base, a foundation, a concealer, a face powder, a control color, a sunscreen cosmetic, a lipstick, a cheek rouge, a lip balm, a lip color, a lip gloss, an eye shadow, an eyeliner, a mascara, a cheek color, a nail polish, a body powder, a perfume powder, and a baby powder, a skin care cosmetic, a hair care cosmetic, and the like. In view of maximizing the light-transmitting effect in the warm color range and the concealing strength of the pigment of the present invention, it is preferable to use the pigment of the present invention in a makeup cosmetic to be applied to a skin.

In addition to the above-described ingredients, the cosmetic of the present invention may contain other ingredients depending on the purpose of the cosmetic, as long as they do not impair the effects of the present invention in terms of quantity and quality. For example, oily components, dyes, pH adjusters, moisturizers, thickeners, surfactants, dispersants, stabilizers, colorants, preservatives, antioxidants, sequestering agents, astringents, anti-inflammatory agents, UV absorbers, fragrances, some pharmaceuticals, and the like can be appropriately added depending on the purpose.

The pigment of the present invention can be used in fields other than cosmetics, such as resin compositions, paints, and inks. In other words, a resin composition, a paint, and an ink containing the pigment of the present invention are each one aspect of the present invention. From another point of view, use of the pigment of the present invention in a resin composition, a paint, or an ink is also an aspect of the present invention. Further, for example, use of the pigment of the present invention for manufacturing a resin composition, a paint, or an ink can be said to be an aspect of the present invention.

The pigment of the present invention can be used as one of materials of a resin composition. Specific examples of uses of a resin composition containing the pigment of the present invention include, but are not limited to, sunroofs, containers made of resin, etc. As the resin, either a thermoplastic resin, such as polyethylene or polypropylene, or a thermosetting resin, such as polycarbonate, may be used. The resin composition is produced by a known method. For example, a resin composition containing the pigment of the present invention can be obtained by dispersing a monomer and the pigment of the present invention in a solvent such as an organic solvent and water, adding a polymerization initiator, heating, washing, and drying. Also, flame retardants, fillers, and the like can optionally be used. The pigment of the present invention is added such that the amount thereof is in the range of preferably 1 g/kg or more and 350 g/kg or less in the obtained resin composition, but the range is not limited to this. By using the pigment of the present invention, it is possible to obtain a white resin composition tinged with warm color.

The pigment of the present invention can be used as one of materials of a paint. Specific examples of uses of a paint containing the pigment of the present invention include, but are not limited to, a residential paint for cold districts. The pigment of the present invention can be used in both water-based and oil-based paints. The paint can be obtained from a resin such as an acrylic resin, a urethane resin, and polyvinyl alcohol, a solvent such as toluene, ethanol, and water, and a colorant represented by the pigment of the present invention. The paint can be produced by a known method. For example, a paint containing the pigment of the present invention can be obtained by adding a curing agent to a resin, then adding the pigment obtained by the present invention and a solvent, and stirring the mixture. Anti-settling agents, preservatives, other pigments, and the like may optionally be used in combination. The pigment of the present invention is added such that the amount thereof is in the range of preferably 1 g/kg or more and 700 g/kg or less in the dried paint film after use, but the range is not limited to this. By using the pigment of the present invention, it is possible to obtain a residential paint that preferentially transmits light in the warm color range, thereby making it easier to raise the indoor temperature.

The pigment of the present invention can be used in an ink. Specific examples of uses of an ink containing the pigment of the present invention include, but are not limited to, a special ink for printing on films, glass surfaces, and the like. The ink can be obtained from a colorant represented by the pigment obtained by the present invention, a resin such as an acrylic resin, and a solvent such as a ketone, a hydrocarbon, and water. The ink is produced by a known method. For example, the ink can be obtained by dispersing and mixing a colorant, a resin, and a solvent. Also, pH adjusters, a surfactant, an antiseptic, a pigment other than the pigment obtained in the present invention, and the like may optionally be used. The pigment of the present invention is added such that the amount thereof is in the range of preferably 1 g/kg or more and 600 g/kg or less in the obtained ink, but the range is not limited to this. By using the pigment of the present invention, it is possible to print on a transparent substrate such as vinyl or glass to give an aesthetic appearance not found in conventional white pigments.

In addition to the above, the pigment of the present invention can be used in applications such as paper, toner external additives, applicators, textile products, packaging materials, films, and coating materials.

Prior to describing the examples, the test methods used in the present invention will be described.

(Diameter or Longest Axis Length of Portion Lighter in Color than Surroundings, and Number Thereof Per Area)

Figure 4:
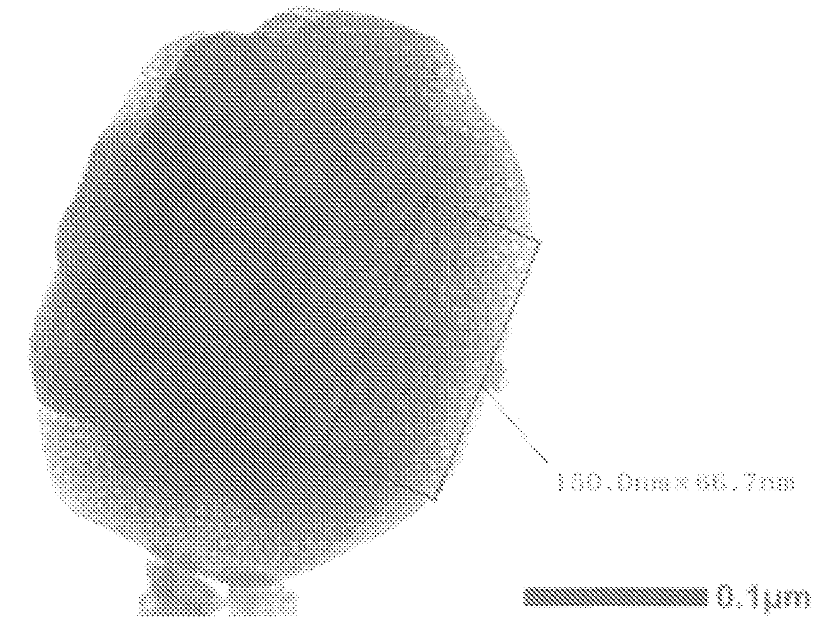
FIG. 4 is a transmission electron micrograph of the pigment obtained in Example 5 on which a rectangular box having an area of $1.0 \times 10^4$ nm$^2$ is drawn.

Using a transmission electron microscope JEM-1400plus manufactured by JEOL Ltd. (hereinafter referred to as "TEM"), the pigment was photographed at an acceleration voltage of 100 kV and a magnification of 100,000×. Among the particles in the photograph other than particles overlapping other particles and particles with a large thickness that make it difficult to count speckled marks, particles that were showing the same appearance as the surrounding particles were brought into focus as much as possible. The contrast of the selected particles was improved, and then those particles were photographed. A rectangular box with an area of 1.0×10 4 $nm^2$ was drawn on the photograph of the selected particles, as illustrated in FIG. 4. In the region within the frame, the diameter or longest axis length of light-colored portions present in a speckled manner having an approximately circular or approximately elliptical outline were measured. The same operation was performed on 10 or more particles, and the number average value (number average diameter) as well as the maximum value (greatest diameter) of the diameters or longest axis lengths of the light-colored portions that are present in a speckled manner and that have a diameter or longest axis length in the range of 1.5 nm or more and 15.0 nm or less were recorded. When the speckles were connected to each other, the diameter of the speckles whose outer diameter can be observed more than half was estimated from the particle outer diameter. Further, the number of light-colored speckled portions having a diameter or longest axis length in the range of 1.5 nm or more and 15.0 nm or less within the frame of 1.0×10 4 $nm^2$ was visually counted. As used herein, "light-colored portion" refers to portions appearing as a lighter color than the surroundings (generally appearing as white or light gray as compared with dark gray or black) that are generally widely distributed in the calcium-titanium composite oxide particles in the pigment of the present invention. The light-colored portions can be observed as generally appearing as approximately circular or elliptical speckles in the particles of the present invention. Errors in the TEM photographs due to the equipment or instruments used for evaluation and unusual white spots in particles that have a distinctly different appearance from other surrounding particles due to local foreign matter and particle defects, etc., are not included in the term "light-colored portion" as used in the present invention.

In addition, when the whole particle was observed at a magnification of 100,000× by the above method but no light-colored portions appeared as speckles, it was determined that no speckled marks were present in the particle.

(True Density)

Measurement was performed according to the JIS K 5101-11-1:2004 A method. As a pycnometer, a 50 mL pycnometer model 055520-050 manufactured by Sibata Scientific Technology, Ltd. was used, and as a replacement liquid, SAJ special grade kerosene manufactured by Sigma-Aldrich Japan was used. A 2 g dried product was used as a sample, and the true density was measured by adjusting the temperature to 25° C.

(Width of Particle Size Distribution)

The width of the particle size distribution was measured by a method according to JIS Z 8825:2013 using a laser beam diffraction scattering particle size analyzer, Microtrac (registered trademark) MT3300EX II, manufactured by MicrotracBEL Corp. Deionized water was used as the dispersion medium. An appropriate amount of the pigment was added dropwise into an ultrasonic dispersing tank of an automatic sample circulator attached to the analyzer, and then ultrasonication for dispersing was performed at an output of 40 W for 360 seconds. After that, as the measurement parameters, the refractive index of the deionized water was set to 1.33, the light transmittance of the particles to be measured was set to "reflect", and the measurement time was set to 30 seconds. The particle size (X10) corresponding to 10% of the cumulative particle size distribution (by volume) and the particle size (×90) corresponding to 90% of the cumulative particle size distribution (by volume) were measured, and ×90/×10 was used as the width of the particle size distribution.

(Particle Size)

The particle size was calculated by $2\times(S/\pi)^{\wedge 0.5}$, where S is the area of the particle when projected in two dimensions, and R is equivalent circle diameter of equal area. The area S of the particle was calculated by photographing the particle with a TEM at an observation magnification of 10,000× and using image analysis software ImageJ. The particle size was the average value of R for 200 or more particles.

(XRD Titanium Oxide Integrated Diffraction Intensity)

Using the X-ray diffractometer RINT-TTR III, manufactured by Rigaku Corporation, X-ray diffractometry was carried out by a powder method. The sample was ground in a mortar and packed in a cell in an amount of about 1.5 g±0.2 g. The start angle was 5.0000°, the end angle was 90.0000°, the sampling width was 0.0100°, the scan speed was 10.0000°/min, the divergence slit was 0.5°, the scattering slit was 0.5°, and the width of the receiving slit was 0.15 mm. For characteristic X-rays, copper was used for the cathode and the wavelength was 0.15418 nm. The obtained X-ray diffraction pattern was subjected to background processing, smoothing, and peak detection using powder X-ray analysis software PDXL2 by Rigaku Corporation. The integrated diffraction intensity of the diffraction line of the (1 2 1) plane appearing in the range of a diffraction angle 20 of 32.50° or more and 33.50° or less was defined as 100.0, and the ratio of the integrated diffraction intensity of the diffraction line appearing in the range of a diffraction angle 20 of 24.75° or more and 28.00° or less to the integrated diffraction intensity of the diffraction line of the (1 2 1) plane appearing in the range of a diffraction angle 20 of 32.50° or more and 33.50° or less was calculated. The calculated ratio was taken as the XRD titanium oxide integrated diffraction intensity.

(Warm Color Light-Transmitting Effect)

3 mL of a styrenated alkyd resin and 0.3 g of pigment were kneaded to form a paint using an H3-type Automatic Hoover Muller manufactured by Toyo Seiki Seisaku-sho, Ltd., and the resulting dispersion was applied to a black-and-white test paper for the concealment rate test, JIS-K5600-4-1, with a 3 mil doctor blade and baked at 130° C. for 30 minutes to obtain a test sample. On the test sample on the black background, the reflection rates in a wavelength in the range of 380 nm or more and 780 nm or less were measured using a spectral color difference meter SQ-2000 manufactured by Nippon Denshoku Industries Co., Ltd (hereinafter referred to as "color difference meter"). The transmittance at each wavelength was calculated by subtracting the found value from 100%. The sum of the transmittances in a wavelength in the range of 380 nm or more and 780 nm or less was taken as the total amount of transmitted light, the sum of the transmittances in a wavelength in the range of 570 nm or more and 780 nm or less was taken as the amount of warm color transmission light, and the value of the amount of warm color transmission light/the total amount of transmission light was taken as the warm color light-transmitting effect.

(Concealment Rate)

The concealment rate, which is an index of the pigment's concealing strength, was obtained by using a color difference meter to measure a lightness index $L_b$ on the black background and a lightness index $L_w$ on the white background of a test sample prepared by the method described in the above section describing the warm color light-transmitting effect, and $L_b/L_w$ was taken as the concealment rate.

EXAMPLES

The present invention will be specifically described below by way of examples, but the following examples are merely for illustrative purposes, and the scope of the invention is not limited by these.

In the stirring operation in the examples and comparative examples, taking properties related to the behavior of the liquid during stirring, such as the amount of liquid, the viscosity of the liquid, and the shape of the container, into consideration, the rotation speed for stirring was adjusted appropriately so that the entire liquid was uniformly mixed and that droplets are not scattered around. For chemicals such as sodium hydroxide, the company name of the manufacturer and distributor thereof will be omitted, in the case where the same effect can be obtained by using any company's product as long as it is a general commercially available product.

Example 1: Rectangular Parallelepiped Particles

Metatitanic acid obtained by a sulfuric acid method was subjected to a deironization and bleaching treatment, and then an aqueous solution of sodium hydroxide was added to adjust the pH to 9.0 to carry out desulfurization. Then, hydrochloric acid was added until the pH reached 5.8 to carry out neutralization. The resultant solution was filtered, and the filter cake was washed to obtain a metatitanic acid cake (hydrolyzate of a titanium compound) having a sulfur content of 9.3 g/kg in terms of $SO_3$. Water was added to the washed cake to prepare a slurry of 2.13 mol/L in terms of Ti, then hydrochloric acid was added to adjust the pH to 1.4. A deflocculation treatment was then carried out to obtain an acid deflocculant of a hydrolyzate of a titanium compound (deflocculant of metatitanic acid). The slurry after the treatment in an amount of 2.25 mol in terms of $TiO_2$ was collected and placed in a reaction vessel with a capacity of 3000 mL. Calcium hydroxide was added thereto such that the mole of calcium, Ca, was 1.15 times the mole of titanium, Ti. 0.36 mol of sodium hydroxide was added thereto, and water was added such that the total volume became 2.0 L. The mixed solution was stirred for 30 minutes using HEIDON600G manufactured by Shinto Scientific Co., Ltd.

The slurry was heated to 95° C. using a B-E type mantle heater manufactured by Tokyo Technological Labo co., LTD. while further stirring and mixing the slurry. Stirring was continued for 18 hours to complete the reaction (atmospheric pressure heating reaction). The stirred slurry was allowed to cool to 50° C., hydrochloric acid was added until the pH reached 5.0, and stirring was continued for additional one hour (calcium removal treatment). The resulting precipitate was washed by decantation, separated by filtration, and dried in air at 120° C. for 10 hours using a Perfect Oven PHH-202 manufactured by ESPEC. CORP. This dried product was fired in air for 1 hour in a Super-C C-2035D manufactured by MOTOYAMA CO., LTD. (hereinafter referred to as "firing furnace") set at 500° C. The fired product was pulverized with an Ishikawa stirring and crushing machine AGA model manufactured by Ishikawa Kojo Co., Ltd. (hereinafter referred to as "automatic mortar") to obtain a white pigment. The particles constituting the pigment mainly had a rectangular parallelepiped shape. When the pigment was evaluated by the test methods described above, it was confirmed that in the transmission electron microscopic image there were portions that were lighter in color than the surroundings are present in a speckled manner. These portions that were lighter in color than the surroundings were circular or elliptical, a maximum diameter or longest axis length was 10.0 nm, and a number average value of the diameter or longest axis length was 4.1 nm. Further, the true density was 3760 $kg/m^3$. In addition, 165 portions having a lighter color than the surroundings were present within the range of $1.0\times10^4$ $nm^2$. The pigment had a particle size of 294 nm, the width of the particle size distribution was 2.25, and the XRD titanium oxide integrated diffraction intensity was 5.23. Moreover, the warm color light-transmitting effect was 0.586, and the concealment rate was 0.731.

Example 2: Rectangular Parallelepiped Particles

A white pigment was obtained by performing atmospheric pressure heating reaction, calcium removal treatment, washing, filtration, drying, and pulverization in the same manner as in Example 1, except that the setting temperature of the firing furnace was changed to 700° C. The shape of the particles constituting the pigment was mainly rectangular parallelepiped. In the transmission electron microscopic image of the pigment, portions lighter in color than the surroundings were confirmed to be present in a speckled manner inside the particles, and were circular or elliptical. The measurement results are shown in Table 2.

Example 3: Rectangular Parallelepiped Particles

A white pigment was obtained by performing atmospheric pressure heating reaction, calcium removal treatment, washing, filtration, drying, and pulverization in the same manner as in Example 1, except that the setting temperature of the firing furnace was changed to 900° C. The shape of the particles constituting the pigment was mainly rectangular parallelepiped. In the transmission electron microscopic image of the pigment, portions lighter in color than the surroundings were confirmed to be present in a speckled manner inside the particles, and were circular or elliptical. The measurement results are shown in Table 2.

Comparative Example 1: Rectangular Parallelepiped Particles

A white pigment was obtained by performing atmospheric pressure heating reaction, calcium removal treatment, washing, filtration, drying, and pulverization in the same manner as in Example 1, except that the firing with the firing furnace was not carried out. The shape of the particles constituting the pigment was mainly rectangular parallelepiped. In the transmission electron microscopic image of the pigment, portions lighter in color than the surroundings were confirmed to be present in a speckled manner inside the particles, and were circular or elliptical. The measurement results are shown in Table 2.

Example 4: Approximately Spherical Particles

A white pigment was obtained by performing atmospheric pressure heating reaction, calcium removal treatment, washing, filtration, drying, firing, and pulverization in the same manner as in Example 1, except that the amount of sodium hydroxide added after adding the calcium hydroxide was changed to 3.60 mol, and that 0.0193 mol of glucose was added per 1 mol of Ca after adding the sodium hydroxide. The shape of the particles constituting the pigment was mainly approximately spherical. In the transmission electron microscopic image of the pigment, portions lighter in color than the surroundings were confirmed to be present in a speckled manner inside the particles, and were circular or elliptical. The measurement results are shown in Table 2.

Example 5: Approximately Spherical Particles

A white pigment was obtained by performing atmospheric pressure heating reaction, calcium removal treatment, washing, filtration, drying, and pulverization in the same manner as in Example 4, except that the setting temperature of the firing furnace was changed to 700° C. The shape of the particles constituting the pigment was mainly approximately spherical. In the transmission electron microscopic image of the pigment, portions lighter in color than the surroundings were confirmed to be present in a speckled manner inside the particles, and were circular or elliptical. The measurement results are shown in Table 2.

Example 6: Approximately Spherical Particles

A white pigment was obtained by performing atmospheric pressure heating reaction, calcium removal treatment, washing, filtration, drying, and pulverization in the same manner as in Example 4, except that the setting temperature of the firing furnace was changed to 900° C. The shape of the particles constituting the pigment was mainly approximately spherical. In the transmission electron microscopic image of the pigment, portions lighter in color than the surroundings were confirmed to be present in a speckled manner inside the particles, and were circular or elliptical. The measurement results are shown in Table 2.

Comparative Example 2: Approximately Spherical Particles

A white pigment was obtained by performing atmospheric pressure heating reaction, calcium removal treatment, washing, filtration, drying, and pulverization in the same manner as in Example 4, except that the firing with the firing furnace was not carried out. The shape of the particles constituting the pigment was mainly approximately spherical. In the transmission electron microscopic image of the pigment, portions lighter in color than the surroundings were confirmed to be present in a speckled manner inside the particles, and were circular or elliptical. The measurement results are shown in Table 2.

Comparative Example 3: Commercially Available Product

A commercially available calcium-titanium composite oxide reagent $CAFO_4PB$ manufactured by Kojundo Chemical Lab. Co., Ltd. was used for Comparative Example 3. The appearance of the reagent was light pink. In the transmission electron microscopic image, the color inside the particles was almost uniform, and speckled marks could not be confirmed. The measurement results are shown in Table 2.

Table 1 shows the production conditions of the pigments of the examples and comparative examples, and Table 2 shows the measurement results of the properties of the pigments obtained in the examples and comparative examples.

As shown in Table 2, the pigments containing particles comprising a calcium-titanium composite oxide as a main component, which can be confirmed to have speckles that are lighter in color than the surroundings in the transmission electron microscopic image, had a greater effect of transmitting warm light, as compared with the pigment (Comparative Example 3) in which no speckled marks could be confirmed. Further, it can also be seen that the pigments having a true density of 3500 kg/m$^3$ or more and 3790 kg/m$^3$ or less has a greater concealing strength, in comparison with the pigments having particles with the same particle shape (comparison between Examples 1 to 3 and Comparative Example 1, and between Examples 4 to 6 and Comparison Example 2). It can be said that these pigments preferentially transmit light in the warm color region and have a high concealing strength.

Thus, it can be said that the pigment of the present invention preferentially transmits light in the warm color region and has a high concealing strength. By using the pigment of the present invention as a raw material for cosmetics, it is possible to obtain cosmetics that have a natural finish and a high concealing strength.

TABLE 1

| | Amount of deflocculated slurry [1) ] mol | Amount of calcium added with respect to titanium mol/mol | Amount of sodium hydroxide added mol/L | Amount of glucose added [2)] mol/mol | Holding time of heating and stirring h | Drying temperature ° C. | Drying time h | Firing temperature ° C. | Firing time h |
|---|---|---|---|---|---|---|---|---|---|
| Example 1 | 2.25 | 1.15 | 0.18 | 0.0000 | 18 | 120 | 10 | 500 | 1 |
| Example 2 | 2.25 | 1.15 | 0.18 | 0.0000 | 18 | 120 | 10 | 700 | 1 |
| Example 3 | 2.25 | 1.15 | 0.18 | 0.0000 | 18 | 120 | 10 | 900 | 1 |
| Comparative Example 1 | 2.25 | 1.15 | 0.18 | 0.0000 | 18 | 120 | 10 | — | — |
| Example 4 | 2.25 | 1.15 | 1.80 | 0.0193 | 18 | 120 | 10 | 500 | 1 |
| Example 5 | 2.25 | 1.15 | 1.80 | 0.0193 | 18 | 120 | 10 | 700 | 1 |
| Example 6 | 2.25 | 1.15 | 1.80 | 0.0193 | 18 | 120 | 10 | 900 | 1 |
| Comparative Example 2 | 2.25 | 1.15 | 1.80 | 0.0193 | 18 | 120 | 10 | — | — |
| Comparative Example 3 [3)] | — | — | — | — | — | — | — | — | — |

1) Amount calculated in terms of $TiO_2$.

2) Mole of glucose with respect to mole of calcium added during atmospheric pressure heating reaction.

3) Commercially-available produce was purchased, and thus the production conditions are not known.

TABLE 2

| | Particle shape | Max. dia. of light-colored portion (num. avg..dia.) nm | True density kg/m$^3$ | Number of light-colored portions per unit area number/ $1.0 \times 10^4$ nm$^2$ | Particle size nm | Width of particle size distribution | XRD titanium oxide integrated diffraction intensity | Warm color light-transmitting effect | Concealment rate |
|---|---|---|---|---|---|---|---|---|---|
| Example 1 | Rectangular parallelepiped | 10.0 (4.1) | 3760 | 166 | 294 | 2.25 | 5.23 | 0.586 | 0.731 |
| Example 2 | Rectangular parallelepiped | 12.0 (3.6) | 3790 | 199 | 285 | 1.61 | 3.34 | 0.589 | 0.732 |

TABLE 2-continued

| | Particle shape | Max. dia. of light-colored portion (num. avg..dia.) nm | True density kg/m³ | Number of light-colored portions per unit area number/ $1.0 \times 10^4$ nm² | Particle size nm | Width of particle size distribution | XRD titanium oxide integrated diffraction intensity | Warm color light-transmitting effect | Concealment rate |
|---|---|---|---|---|---|---|---|---|---|
| Example 3 | Rectangular parallelepiped | 15.0 (3.4) | 3750 | 115 | 336 | 2.12 | 2.40 | 0.586 | 0.748 |
| Comparative Example 1 | Rectangular parallelepiped | 7.0 (2.9) | 3930 | 209 | 324 | 2.81 | 6.07 | 0.593 | 0.727 |
| Example 4 | Approximately spherical | 10.0 (2.6) | 3640 | 189 | 283 | 2.75 | 1.81 | 0.593 | 0.694 |
| Example 5 | Approximately spherical | 10.0 (3.8) | 3540 | 191 | 274 | 2.27 | 2.02 | 0.596 | 0.694 |
| Example 6 | Approximately spherical | 10.0 (3.2) | 3530 | 127 | 269 | 2.54 | 1.98 | 0.598 | 0.729 |
| Comparative Example 2 | Approximately spherical | 12.5 (4.4) | 3800 | 88 | 302 | 2.71 | 3.14 | 0.589 | 0.684 |
| Comparative Example 3 | Approximately spherical | none | 4310 | none | 715 | 13.19 | 3.72 | 0.536 | 0.656 |

Next, powder foundations produced by using the pigments obtained in the examples and comparative examples were subjected to a sensory evaluation by the following method.

(Sensory Evaluation of Powder Foundation)

Each pigment obtained in the examples and comparative examples was subjected to a surface treatment with methylhydrogenpolysiloxane, and the ingredients were uniformly mixed according to the formulation shown in Table 3 using a LAB. Mixer LM-110T manufactured by HANIL Electric. Co., Lid (hereinafter referred to as "mixer"). The mixture was pulverized using a sample mill TASM-1 manufactured by Tokyo Atomizer M.F.G. Co., Ltd. (hereinafter referred to as "sample mill"). A predetermined amount of the resultant was then filled in a metal plate and compression molded to produce a powder foundation.

TABLE 3

| Ingredient | Amount added (g/kg) |
|---|---|
| Pigment obtained from example or comparative example after surface treatment with methylhydrogenpolysiloxane | 100.0 |
| Mica | 300.0 |
| Talc | 481.2 |
| Coloring pigment | 18.8 |
| Squalane | 100.0 |

Ten panelists applied each of the obtained powder foundations on their arms and faces, especially on areas with dullness, spots, etc., and the natural finish and concealing strength were evaluated.

(Natural Finish)

The impression from a visual comparison with areas where foundation was not applied was evaluated according to the following criteria, and whether or not a "natural finish" was achieved was determined based on the average score of the 10 panelists. A higher score means that the foundation had less "white cast" and achieved a "natural finish". Table 4 shows the results of the sensory evaluation.

(Evaluation Criteria)

4 points: Indistinguishable from non-applied areas even when viewed at close range (30 cm).

3 points: Fact that powder foundation had been applied could be seen when viewed at close range, but looked natural.

2 points: Looked white when viewed at close range.

1 point: Looked white even when viewed from a distant position (1 m).

(Concealing Strength)

The impression when the foundations were applied on spots and dullness was evaluated according to the following criteria, and "concealing strength" was evaluated based on the average score of the 10 panelists. A higher score means that the foundation had better concealing strength. Table 4 shows the results of the sensory evaluation.

(Evaluation Criteria)

4 points: Spots and dullness could not be seen even when viewed at close range (30 cm).

3 points: Spots and dullness could be seen when viewed from close range, but were not noticeable.

2 points: Spots and dullness could be seen when viewed from close range.

1 point: Distance from which spots and dullness could be seen did not change from when foundation was not applied.

(Criteria of Overall Evaluation)

Total of points for natural finish and points for concealing strength:

7 or more: A 5 points or more and less than 7 points:

3 points or more and less than 5 points:

less than 3 points:

TABLE 4

| Sensory test item | Particle size | Natural finish | Concealing strength | Overall evaluation |
|---|---|---|---|---|
| Example 1 | Rectangular parallelepiped | 3 | 4 | A |
| Example 2 | Rectangular parallelepiped | 3 | 4 | A |
| Example 3 | Rectangular parallelepiped | 3 | 4 | A |
| Comparative Example 1 | Rectangular parallelepiped | 3 | 3 | B |
| Example 4 | Approximately spherical | 4 | 2 | B |
| Example 5 | Approximately spherical | 4 | 2 | B |

TABLE 4-continued

| Sensory test item | Particle size | Natural finish | Concealing strength | Overall evaluation |
|---|---|---|---|---|
| Example 6 | Approximately spherical | 4 | 3 | A |
| Comparative Example 2 | Approximately spherical | 3 | 1 | C |
| Comparative Example 3 | Approximately spherical | 1 | 1 | D |

As a result of the sensory evaluation, it was found that the foundations produced using a pigment containing particles having speckled marks as a main component had a natural finish with little white cast. Further, it was found that compared with pigments having the same particle shape (comparison between Examples 1 to 3 and Comparative Example 1, and comparison between Examples 4 to 6 and Comparative Examples 2 and 3), the pigment of the present invention had greater concealing strength than the pigments of the comparative examples. In addition, the pigments of Examples 4 to 6, in which the particles were approximately spherical, had a smoother feel than those in which the particles were in the shape of a rectangular parallelepiped. By incorporating the pigment of the present invention into a cosmetic, it was possible to provide the cosmetic that can produce a natural finish and that also has excellent concealing strength.

Example 7

(Manufacture of Powder Foundation)

The ingredients 1 to 13 below were mixed and uniformly pulverized (step A). Then, ingredients 15 to 17 were uniformly mixed and added to the pulverized mixture obtained in step A to obtain a uniform mixture (step B). Ingredient 14 was then added thereto, and the resulting mixture was press-molded in a mold to obtain a powder foundation (step C).

It was confirmed that the obtained powder foundation did not cause white cast when applied to a skin, provided a finish that looked like a natural bare skin, and had a good concealing strength.

| (Ingredients) | compound ratio (g/kg) |
|---|---|
| 1. Caprylyl silane-treated mica (Note 1) | 400 |
| 2. Caprylyl silane-treated pigment described in Example 6 (Note 1) | 50 |
| 3. Silicone-treated talc (Note 2) | balance |
| 4. Silicone-treated, pigment-grade titanium oxide (Note 2) | 50 |
| 5. Silicone-treated titanium dioxide fine particle (Note 2) | 50 |
| 6. Silicone-treated barium sulfate (Note 2) | 100 |
| 7. Silicone-treated red iron oxide (Note 2) | 4 |
| 8. Silicone-treated yellow iron oxide (Note 2) | 20 |
| 9. Silicone treated amber (Note 2) | 4 |
| 10. Silicone-treated black iron oxide (Note 2) | 1 |
| 11. Phenyl-modified hybrid silicone composite powder (Note 3) | 20 |
| 12. Spherical polymethylsilsesquioxane powder (Note 4) | 5 |
| 13. Preservative | appropriate amount |
| 14. Fragrance | appropriate amount |
| 15. Crosslinked dimethylpolysiloxane (Note 5) | 40 |
| 16. Glyceryl trioctanoate | 20 |
| 17. Squalane | 10 |

(Note 1)
Surface treated with AES-3083 manufactured by Shin-Etsu Chemical Co., Ltd.
(Note 2)
Surface treated with KF-9909 manufactured by Shin-Etsu Chemical Co., Ltd.
(Note 3)
KSP-300 manufactured by Shin-Etsu Chemical Co., Ltd.
(Note 4)
KMP-590 manufactured by Shin-Etsu Chemical Co., Ltd.
(Note 5)
KSG-16 manufactured by Shin-Etsu Chemical Co., Ltd.

Example 8

(Manufacture of Pressed Powder)

The ingredients 1 to 7 below were mixed and pulverized (step A). The mixed pulverized product was then transferred to a mixer, ingredients 8 to 12 were added, and they were stirred and mixed so as to become uniform (step B). The mixture was then pulverized using a sample mill, and the resultant was press-molded in an aluminum plate to obtain a pressed powder (step C).

It was confirmed that the obtained pressed powder did not cause white cast when applied to a skin, provided a finish that looked like a natural bare skin, and had a good concealing strength.

| (Ingredients) | compound ratio (g/kg) |
|---|---|
| 1. Talc | balance |
| 2. PMMA (Note 1) | 100 |
| 3. Sericite | 300 |
| 4. Scaly silica (Note 2) | 30 |
| 5. Pigment described in Example 4 | 60 |
| 6. Preservative | appropriate amount |
| 7. Color material | appropriate amount |
| 8. Octyl methoxycinnamate | 30 |
| 9. Squalane | 20 |
| 10. Preservative | appropriate amount |
| 11. Antioxidant | appropriate amount |
| 12. Fragrance | appropriate amount |

(Note 1)
Matsumoto Microsphere M-100, 7 μm product, manufactured by Matsumoto Yushi-Seiyaku Co., Ltd.
(Note 2)
Sun Lovely C manufactured by Dokai Chemical Industry Co., Ltd.

Example 9

(Manufacture of Loose Powder)

The ingredients 1 to 7 below were mixed and pulverized (step A). The mixed pulverized product was then transferred to a mixer, ingredients 8 to 10 were added, and they were stirred and mixed so as to become uniform (step B). The mixture obtained in step B was further pulverized using a sample mill and packed to obtain a loose powder (step C).

It was confirmed that the obtained loose powder did not cause white cast when applied to a skin, provided a finish that looked like a natural bare skin, and had a good concealing strength.

| (Ingredients) | compound ratio (g/kg) |
|---|---|
| 1. Talc | balance |
| 2. Pigment described in Example 3 | 10 |
| 3. Amihope LL | 30 |
| 4. PMMA (Note 1) | 80 |
| 5. Preservative | appropriate amount |
| 6. Color material | appropriate amount |
| 7. Squalane | 10 |
| 8. Preservative | appropriate amount |
| 9. Antioxidant | appropriate amount |
| 10. Fragrance | appropriate amount |

(Note 1)
Matsumoto Microsphere S-100, 10 μm product, manufactured by Matsumoto Yushi-Seiyaku Co., Ltd.

Example 10

(Manufacture of Oily Foundation)

The ingredients 1 to 6 below were mixed in a mixer and pulverized uniformly (step A). Then, ingredients 7 to 16 were heated to 85° C. to dissolve, the mixed pulverized product obtained in step A was added thereto, and the resultant was stirred uniformly (step B). The mixture was defoamed, and then the solids were poured into a tray and slowly cooled to room temperature to obtain an oily foundation (step C).

It was confirmed that the obtained oily foundation did not cause white cast when applied to a skin, provides a finish that looked like a natural bare skin, and had a good concealing strength.

| (Ingredients) | compound ratio (g/kg) |
|---|---|
| 1. Silicone-treated talc (Note 1) | 53 |
| 2. Silicone treated pigment described in Example 4 (Note 1) | 150 |
| 3. Silicone-treated sericite (Note 1) | 282 |
| 4. Silicone-treated red iron oxide (Note 1) | 5 |
| 5. Silicone treated yellow iron oxide (Note 1) | 18 |
| 6. Silicone-treated black iron oxide (Note 1) | 2 |
| 7. Candelilla wax | 10 |
| 8. Carnauba wax | 10 |
| 9. Ceresin | 15 |
| 10. Decamethylcyclopentasiloxane | 140 |
| 11. Isononyl isononanoate | balance |
| 12. Polyglyceryl diisostearate | 20 |
| 13. Dextrin palmitate | 10 |
| 14. Octyl methoxycinnamate | 30 |
| 15. Preservative | appropriate amount |
| 16. Antioxidant | appropriate amount |

(Note 1)
Surface treated with KF-96A-50cs manufactured by Shin-Etsu Chemical Co., Ltd.

Example 11

(Manufacture of Stick Foundation)

The ingredients 12 to 16 below were mixed in a mixer (step A). Further, ingredients 1 to 11 were weighed into a container capable of holding the entire amount, and heated to 85° C. to dissolve (step B). In addition, ingredients 17 to 21 were weighed into a separate container and dissolved (step C). Then, the mixture obtained in step A was added to the thermally-dissolved mixture obtained in step B and dispersed therein using a stirrer until the resulting mixture became visually uniform, and the thermally-dissolved mixture obtained in step C was further added thereto to emulsify (step D). The mixture was defoamed, and the solids were then poured into a mold and slowly cooled to room temperature to obtain a stick foundation (step E).

It was confirmed that the obtained stick foundation did not cause white cast when applied to a skin, provided a finish that looked like a natural bare skin, and had a good concealing strength.

| (Ingredients) | compound ratio (g/kg) |
|---|---|
| 1. Dimethyl polysiloxane | 180 |
| 2. Decamethylcyclopentasiloxane | 300 |
| 3. Octyl methoxycinnamate | 50 |
| 4. Diisostearyl malate | 40 |
| 5. Candelilla wax | 60 |
| 6. Hydrogenated jojoba ester | 40 |
| 7. Cetyl dimethicone copolyol | 20 |
| 8. Sorbitan sesquiisostearate | 5 |
| 9. Antioxidant | appropriate amount |
| 10. Preservative | appropriate amount |
| 11. Fragrance | appropriate amount |
| 12. Silicone-treated coloring agent (Note 1) | 5 |
| 13. Silicone-treated pigment described in Example 1 (Note 1) | 85 |
| 14. Silicone-treated talc (Note 1) | 60 |
| 15. Silicone-treated mica (Note 1) | 20 |
| 16. Polymethyl methacrylate | 20 |
| 17. Purified water | balance |
| 18. Sodium citrate | 3 |
| 19. 1,3-Butylene glycol | 30 |
| 20. Glycerin | 20 |
| 21. Preservative | appropriate amount |

(Note 1)
Surface treated with KF-99P manufactured by Shin-Etsu Chemical Co., Ltd.

Example 12

(Manufacture of W/O Emulsified Foundation)

The ingredients 12 to 14 below were stirred and mixed using a mixer (step A), and then ingredients 1 to 11 were added and dispersed therein using a stirrer until the resulting mixture became visually uniform (step B). Ingredients 15 to 19 were heated and dissolved in a separate container (step C). Then, the thermally-dissolved mixture obtained in step C was added to the dispersion obtained in step B to emulsify, and then cooled to room temperature to obtain a W/O emulsified foundation (step D).

It was confirmed that the obtained W/O emulsified foundation did not cause white cast when applied to a skin, provided a finish that looked like a natural bare skin, and had a good concealing strength.

| (Ingredients) | compound ratio (g/kg) |
|---|---|
| 1. POE modified silicone (Note 1) | 8 |
| 2. Polyglyceryl polyricinoleate | 5 |
| 3. Neopentyl glycol dicaprate | 30 |
| 4. Squalane | 10 |
| 5. Pentaerythrityl tetraoctanoate | 20 |
| 6. Inulin stearate (Note 2) | 10 |
| 7. Octyl methoxycinnamate | 40 |
| 8. Decamethylcyclopentasiloxane | 154 |
| 9. Preservative | appropriate amount |
| 10. Antioxidant | appropriate amount |
| 11. Fragrance | appropriate amount |
| 12. Silicone-treated pigment described in Example 5 (Note 3) | 80 |
| 13. Silicone-treated talc (Note 3) | 57 |
| 14. Silicone-treated coloring agent (Note 3) | 10 |
| 15. Purified water | balance |
| 16. 1,3-Butylene glycol | 60 |

-continued

| (Ingredients) | compound ratio (g/kg) |
|---|---|
| 17. Glycerin | 10 |
| 18. Sodium chloride | 10 |
| 19. Preservative | appropriate amount |

(Note 1)
Product with an HLB value of 4.5
(Note 2)
Rheopearl (registered trademark) ISK manufactured by Chiba Flour Milling Co., Ltd.
(Note 3)
Surface treated with KF-9901 manufactured by Shin-Etsu Chemical Co., Ltd.

Example 13

(Manufacture of O/W Emulsified Foundation)

Ingredients 1 to 7 were heated at 85° C. to dissolve (step A). Separately, ingredients 8 to 10 were mixed and pulverized (step B). Further separately, ingredients 11 to 15 were heated to 85° C. to obtain a dissolved mixture (step C). Then, the pulverized mixture obtained in step B was added to the thermally-dissolved mixture obtained in step A, and dispersed therein using a stirrer until the resulting mixture became visually uniform. The thermally-dissolved mixture obtained in step C was gradually added thereto to emulsify, and the emulsified mixture was cooled to room temperature while stirring. Next, the cooled mixture was filled into an appropriate container to obtain an O/W emulsified foundation (step D).

It was confirmed that the O/W emulsified foundation did not cause white cast when applied to a skin, provided a finish that looked like a natural bare skin, and had a good concealing strength.

| (Ingredients) | compound ratio (g/kg) |
|---|---|
| 1. Stearic acid | 4 |
| 2. Isostearic acid | 3 |
| 3. Cetyl 2-ethylhexanoate | 40 |
| 4. Liquid paraffin | 110 |
| 5. Polyoxyethylene (10) stearyl ether | 20 |
| 6. Cetyl alcohol | 3 |
| 7. Preservative | 2 |
| 8. Talc | 150 |
| 9. Coloring agent | 40 |
| 10. Pigment described in Example 1 | 30 |
| 11. Triethanolamine | 4 |
| 12. Propylene glycol | 50 |
| 13. Purified water | 541 |
| 14. Preservative | 2 |
| 15. Antioxidant | 1 |

Example 14

(Manufacture of W/O Liquid Foundation)

The ingredients 8 to 12 below were uniformly mixed (step A). Then, a part of ingredient 4 and ingredient 13 were mixed, and the resultant was added to the mixture obtained in step A, and dispersed therein using a stirrer until the resulting mixture became visually uniform (step B). Separately, ingredients 1 to 3, the rest of ingredient 4, and ingredients 5 to 7 were mixed and dispersed using a stirrer until the resulting mixture became visually uniform (step C). Further separately, ingredients 14 to 18 and ingredient 20 were mixed and dispersed using a stirrer until the resulting mixture became visually uniform (step D). The mixture obtained in step D was gradually added under stirring to the mixture obtained in step C to emulsify, and the dispersion obtained in step B and ingredient 19 were further added thereto to obtain a W/O liquid foundation (step E).

It was confirmed that the obtained W/O liquid foundation did not cause white cast when applied to a skin, provided a finish that looked like a natural bare skin, and had a good concealing strength.

| (Ingredients) | compound ratio (g/kg) |
|---|---|
| 1. Crosslinked polyether-modified silicone (Note 1) | 30 |
| 2. Crosslinked dimethylpolysiloxane (Note 2) | 50 |
| 3. Branched polyether-modified silicone (Note 3) | 20 |
| 4. Decamethylcyclopentasiloxane | 211 |
| 5. Cetyl isooctanoate | 50 |
| 6. Dimethylpolysiloxane (Note 4) | 65 |
| 7. Dimethyl distearyl ammonium hectorite | 12 |
| 8. Silicone-treated pigment described in Example 1 (Note 5) | 50 |
| 9. Silicone-treated pigment-grade titanium oxide (Note 5) | 50 |
| 10. Silicone-treated red iron oxide (Note 5) | 4 |
| 11. Silicone treated yellow iron oxide (Note 5) | 10 |
| 12. Silicone-treated black iron oxide (Note 5) | 1 |
| 13. Acrylic silicone resin solution (Note 6) | 20 |
| 14. 1,3-Butylene glycol | 50 |
| 15. Xanthan gum (Note 7) | 50 |
| 16. Sodium citrate | 2 |
| 17. Sodium chloride | 5 |
| 18. Preservative | appropriate amount |
| 19. Fragrance | appropriate amount |
| 20. Purified water | 320 |

(Note 1)
KSG-210 manufactured by Shin-Etsu Chemical Co., Ltd.
(Note 2)
KSG-15 manufactured by Shin-Etsu Chemical Co., Ltd.
(Note 3)
KF-6028P manufactured by Shin-Etsu Chemical Co., Ltd.
(Note 4)
Product of 6 $mm^2$/sec (25° C.)
(Note 5)
Surface treated with KF-9909 manufactured by Shin-Etsu Chemical Co., Ltd.
(Note 6)
KP-575 manufactured by Shin-Etsu Chemical Co., Ltd.
(Note 7)
Aqueous solution of 20 g/kg.

Example 15

(Manufacture of Sunscreen Cream)

A sunscreen cream was produced in order to confirm the UV-blocking ability of the pigment of the present invention. The ingredient 7 below was added to a part of ingredient 5 to obtain a uniform mixture, and ingredients 8 and 9 were added and dispersed therein using a bead mill (step A). Separately, ingredients 1 to 4, the rest of ingredient 5, and ingredient 6 were uniformly mixed (step B). Further separately, ingredients 10 to 12, and ingredient 14 were dispersed using a stirrer until the resulting mixture became visually uniform (step C). Next, the mixture obtained in step C was added to the mixture obtained in step B to emulsify, and the dispersion obtained in step A and ingredient 13 were added thereto to obtain a sunscreen cream (step D).

It was confirmed that the obtained sunscreen cream had about the same level of high UV-blocking ability as titanium oxide, did not cause white cast when applied to the skin, and provided a finish that looked like the natural bare skin.

| (Ingredients) | compound ratio (g/kg) |
|---|---|
| 1. Crosslinked polyether-modified silicone (Note 1) | 30 |
| 2. Crosslinked dimethylpolysiloxane (Note 2) | 20 |
| 3. Alkyl-modified, branched polyether-modified silicone (Note 3) | 10 |
| 4. Neopentyl glycol dioctanoate | 50 |
| 5. Decamethylcyclopentasiloxane | 175 |
| 6. Octyl methoxycinnamate | 60 |
| 7. Acrylic silicone resin solution (Note 4) | 100 |
| 8. Caprylyl silane-treated zinc oxide fine particle (Note 5) | 200 |
| 9. Caprylyl silane-treated pigment described in Example 2 (Note 5) | 30 |
| 10. 1,3-Butylene glycol | 20 |
| 11. Sodium citrate | 2 |
| 12. Sodium chloride | 5 |
| 13. Fragrance | appropriate amount |
| 14. Purified water | 298 |

(Note 1)
KSG-240 manufactured by Shin-Etsu Chemical Co., Ltd.
(Note 2)
KSG-15 manufactured by Shin-Etsu Chemical Co., Ltd.
(Note 3)
KF-6038 manufactured by Shin-Etsu Chemical Co., Ltd.
(Note 4)
KP-575 manufactured by Shin-Etsu Chemical Co., Ltd.
(Note 5)
Surface treated with AES-3083 manufactured by Shin-Etsu Chemical Co., Ltd.

Example 16

(Manufacture of Resin Composition)

A resin composition containing the pigment of the present invention was produced. Ingredient 1 was distilled and then bubbled with nitrogen for 30 minutes (step A). Ingredient 5 and ingredient 6 were mixed and dispersed using a bead mill (step B). The liquid obtained in step A and ingredients 2 to 4 were added to ingredient 7, and the mixture was heated while stirring. 5 minutes after reaching 65° C., the dispersion obtained in step B was added thereto, and stirring was continued while keeping the temperature at 65° C. (step C). After 10 hours, ingredient 8 was added to neutralize the mixture (step D), which was then filtered and washed to obtain a resin composition (step E).

When the obtained resin composition was held up to sunlight, it was confirmed that the transmitted light had a significantly large ratio of light in the warm color range, and so the resin composition had a warm color light-transmitting effect.

| (Ingredients) | compound ratio (g/kg) |
|---|---|
| 1. Methyl methacrylate | 600 |
| 2. Azoisobutyl nitrile | 0.3 |
| 3. Sodium chloride | 1 |
| 4. Calcium phosphate | 6 |
| 5. Methylhydrogenpolysiloxane surface-treated pigment described in Example 4 | 200 |
| 6. Toluene | 140 |
| 7. Purified water | appropriate amount |
| 8. Hydrochloric acid | appropriate amount |

Example 17

(Manufacture of Paint)

A paint containing the pigment of the present invention was produced. Ingredients 1 to 4 were mixed using a mixer for 30 or more and 120 minutes or less (step A), and then dispersed for 24 hours using a bead mill (step B).

When the obtained paint was applied to a transparent glass substrate and held up to light, it was confirmed that the transmitted light had a significantly large ratio of light in the warm color range, and so the paint had a warm color light-transmitting effect.

| (Ingredients) | compound ratio (g/kg) |
|---|---|
| 1. Acrylic resin (Note 1) | 300 |
| 2. Methylhydrogenpolysiloxane surface-treated pigment described in Example 4 | 300 |
| 3. Toluene | 200 |
| 4. Isophorone | 200 |

(Note 1)
Including polymerization initiator

Example 18

(Manufacture of Ink)

An ink containing the pigment of the present invention was produced. The ingredients 1 to 4 below were mixed using a mixer for 30 or more and 120 minutes or less (step A), and then dispersed for 24 hours using a bead mill (step B).

When the obtained ink was applied to a glass plate and held up to light, it was confirmed that the transmitted light had a significantly large ratio of light in the warm color range, and so the ink had a warm color light-transmitting effect.

| (Ingredients) | compound ratio (g/kg) |
|---|---|
| 1. Acrylic resin | 75 |
| 2. Methylhydrogenpolysiloxane surface-treated pigment described in Example 4 | 495 |
| 3. Methylcyclohexane | 400 |
| 4. Dispersant (Note 1) | 10 |
| 5. Gelling agent (Note 2) | 20 |

(Note 1)
Homogenol (registered trademark) L-18 manufactured by Kao Corporation
(Note 2)
Organite (registered trademark)-T manufactured by Nihon Yuukinendo Co., Ltd.

The invention claimed is:

1. A pigment comprising particles containing a calcium-titanium composite oxide as a main component, wherein
when the particles of the calcium-titanium composite oxide in the pigment are observed in a transmission electron microscopic image at a magnification of 100,000×, at least one area of the image is lighter in color than its surroundings, and
the pigment has a true density of 3500 kg/m$^3$ or more and 3790 kg/m$^3$ or less;
wherein the pigment is produced by:
mixing an acid deflocculant of a hydrolyzate of a titanium compound, an alkali, and a water-soluble compound containing calcium to obtain a mixture, and heating the mixture to 70° C. or higher and 100° C. or lower under atmospheric pressure to produce a reaction product;
cooling the obtained reaction product, followed by allowing to stand at pH 7.0 or less for 1 hour or more;
subjecting the reaction product after allowed to stand to solid-liquid separation to collect a solid; and
firing the solid at 500° C. or higher.

2. The pigment according to claim 1, wherein the areas lighter in color than the surroundings have a circular shape with a diameter of 1.5 nm or more and 15.0 nm or less or an elliptical shape with the longest axis length of 1.5 nm or more and 15.0 nm or less, and 100 or more and 200 or less of the areas lighter in color than the surroundings are present in a range corresponding to $1.0\times10^4$ $nm^2$ on the transmission electron microscopic image.

3. The pigment according to claim 1, wherein the areas lighter in color than the surroundings have a number average of the diameter or the longest axis length of 2.5 nm or more and 4.5 nm or less.

4. The pigment according to claim 1, having a particle size of 200 nm or more and 500 nm or less.

5. The pigment according to claim 1, having a width of a particle size distribution set in JIS Z8825:2013 is smaller than 10.00.

6. The pigment according to claim 1, wherein, when the pigment is measured in X-ray diffractometry, and when an integrated diffraction intensity of a diffraction line of a (1 2 1) plane appearing in a range of a diffraction angle of 32.50° or more and 33.50° or less is defined as 100.0, a ratio of an integrated diffraction intensity of a diffraction line appearing in a range of a diffraction angle of 24.75° or more and 28.00° or less is 12.00 or less.

7. The pigment according to claim 1, wherein a coating layer of an inorganic substance and/or an organic substance is present on at least a part of a surface of the particles.

8. A cosmetic comprising the pigment according to claim 1.

9. A resin composition comprising the pigment according to claim 1.

10. A paint comprising the pigment according to claim 1.

11. An ink comprising the pigment according to claim 1.

12. A method for producing the pigment according to claim 1, the method comprising:

mixing an acid deflocculant of a hydrolyzate of a titanium compound, an alkali, and a water-soluble compound containing calcium to obtain a mixture, and heating the mixture to 70° C. or higher and 100° C. or lower under atmospheric pressure to produce a reaction product;

cooling the obtained reaction product, followed by allowing to stand at pH 7.0 or less for 1 hour or more;

subjecting the reaction product after allowed to stand to solid-liquid separation to collect a solid; and firing the solid at 500° C. or higher.

* * * * *